United States Patent [19]

Martel et al.

[11] Patent Number: 4,801,723
[45] Date of Patent: Jan. 31, 1989

[54] INTERMEDIATES FOR (1,5) 6,6-DIMETHYL-4-HYDROXY-3-OXABICYCLO (3,1,0) HEXAN-2-ONE AND ITS ETHERS

[75] Inventors: Jacques Martel, Bondy; Jean Tessier, Vincennes; Jean-Pierre DeMoute, Montreuil-sous-Bois, all of France

[73] Assignee: Roussel Uclaf, Paris, France

[21] Appl. No.: 36,890

[22] Filed: Apr. 10, 1987

Related U.S. Application Data

[60] Division of Ser. No. 759,477, Jul. 25, 1985, abandoned, which is a division of Ser. No. 582,321, Feb. 22, 1984, abandoned, which is a continuation of Ser. No. 361,780, Mar. 25, 1982, abandoned, which is a continuation of Ser. No. 170,093, Jul. 18, 1980, abandoned.

[30] Foreign Application Priority Data

Jul. 31, 1979 [FR] France .................. 29 19654

[51] Int. Cl.$^4$ ........................... C07D 307/58
[52] U.S. Cl. ................................... 549/313
[58] Field of Search ................ 549/313, 318, 319

[56] References Cited

FOREIGN PATENT DOCUMENTS 1072629 8/1958 Fed. Rep. of Germany ...... 549/313

OTHER PUBLICATIONS

Kaeriyama et al., CA 87:39258M.
Fuchs et al., CA 63:6851a.
CA 63:11352g.
Hashimoto et al., CA 86:71934u.
Merwe et al., CA 62:9088e.

Primary Examiner—Jane T. Fan
Attorney, Agent, or Firm—Bierman and Muserlian

[57] ABSTRACT

A process for the preparation of compounds of the (1RS, 4RS, 5SR), (1R, 4R, 5S) or (1S, 4S, 5R) configuration having the formula

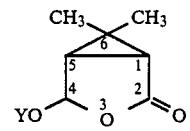

wherein Y is selected from the group consisting of hydrogen and the organic residue Z of an optionally chiral alcohol of the formula ZOH comprising reacting in the presence of an acid agent 5RS-hydroxy-2,5-dihydrofuran-2-one having the formula

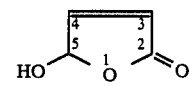

either (a) with an achiral alcohol of the formula ZOH to obtain the resulting ether and reacting the latter in an anhydrous medium with an isopropylidene sulfurane of the formula

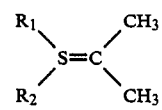

wherein $R_1$ and $R_2$ are individually selected from the group consisting of optionally substituted monocyclic aromatic groups, isopropyl, groups and tertiary alkyl groups, to obtain a compound of formula I of the (1RS, 4RS, 5SR) configuration and Y is Z and optionally hydrolyzing the latter in acid medium to obtain the compound of formula I wherein Y is hydrogen or (b) with an optically active chiral alcohol of the formula ZOH to obtain a mixture of stereoisomeric ether due to the asymetrical carbon in the 5-position which mixture is rich in one of the two diastereoisomers, separating the diastereoisomeric ethers by physical means and reacting the separated diastereoisomers with the compound of formula II in anhydrous medium to obtain the compound of formula I with (1R, 4R, 5S) or (1S, 4S, 5R) configuration wherein Y is Z and optionally hydrolyzing the latter in an acid media to obtain the compound of formula I wherein Y is hydrogen and novel intermediates. The compounds of formula I where Y is hydrogen are described in French Pat. No. 1,580,474 and are interemediates for diversely substituted cyclopropane carboxylic acids whose esters are may active insecticides.

2 Claims, No Drawings

INTERMEDIATES FOR (1,5) 6,6-DIMETHYL-4-HYDROXY-3-OXABICYCLO (3,1,0) HEXAN-2-ONE AND ITS ETHERS

PRIOR APPLICATION

This application is a divisional of copending U.S. patent application Ser. No. 759,477, filed July 25, 1985, now abandoned, which is a divisional application of copending application Ser. No. 582,321, filed Feb. 22, 1984, now abandoned, which in turn is a continuation of copending application Ser. No. 361,780, filed Mar. 25, 1982, now abandoned, which in turn is a continuation of application Ser. No. 170,093, filed July 18, 1980, now abandoned.

OBJECTS OF THE INVENTION

It is an object of the invention to provide an improved process for the preparation of the various stereoisomers of (1,5) 6,6-dimethyl-4-hydroxy-3-oxabicyclo (3,1,0) hexan-2-ones of formula I.

It is another object of the invention to provide novel intermediate compounds.

These and other objects and advantages of the invention will become obvious from the following detailed description.

THE INVENTION

The novel process of the invention for the preparation of compounds of the (1RS, 4RS, 5SR), (1R, 4R, 5S) or (1S, 4S, 5R) configuration having the formula

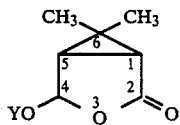

wherein Y is selected from the group consisting of hydrogen and the organic residue Z of an optionally chiral alcohol of the formula ZOH comprises reacting in the presence of an acid agent 5RS-hydroxy-2,5-dihydrofuran-2-one having the formula

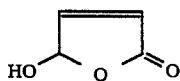

either (a) with an achiral alcohol of the formula ZOH to obtain the resulting ether and reacting the latter in an anhydrous medium with an isopropylidene sulfurane of the formula

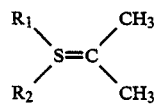

wherein $R_1$ and $R_2$ are individually selected from the group consisting of optionally substituted monocyclic aromatic groups, isopropyl groups and tertiary alkyl groups, to obtain a compound of formula I of the (1RS, 4RS, 5SR) configuration and Y is Z and optionally hydrolyzing the latter in acid medium to obtain the compound of formula I wherein Y is hydrogen or (b) with an optically active chiral alcohol of the formula ZOH to obtain a mixture of stereoisomeric ethers due to the asymetrical carbon in the 5-position which mixture is rich in one of the two diastereoisomers, separating the diastereoisomeric ethers by physical means and reacting the separated diastereoisomers with the compound of formula III in anhydrous medium to obtain the compound of formula I with (1R,4R,5S) or (1S,4S,5R) configuration wherein Y is Z and optionally hydrolyzing the latter in an acid media to obtain the compound of formula wherein Y is hydrogen.

Examples of $R_1$ and $R_2$ are phenyl and phenyl optionally substituted with methyls.

The preferred sulfurane of formula III is diphenyl isopropylidene sulfurane and the sulfuranes of formula III may be prepared by reacting a base with a salt of the corresponding isopropyl sulfonium, preferably a fluoroborate salt.

The acid agent present in the reaction of the alcohol ZOH and the compound of formula II is preferably selected from the group consisting of sulfonic acids, sulfuric acid, hydrochloric acid and phosphoric acid, most preferably p-toluene sulfonic acid. The reaction with the sulfurane of formula III is preferably effected in a solvent selected from the group consisting of dimethyl ether or diethyl ether of diethyleneglycol, ether, dimethylsulfoxide, tetrahydrofuran or dimethoxyethane and especially in tetrahydrofuran and the formation of the cyclopropyl ring is effected at −90° to −30° C.

The optional hydrolysis of the ethers of formula I is preferably effected with a strong acid in the presence of water and a water-miscible solvent capable of dissolving the compound to be hydrolyzed. The strong acid is preferably selected from the group consisting of sulfonic acids, sulfuric acid, hydrochloric acid and phosphoric acid and the solvent is preferably selected from the group consisting of alkanols, dioxane, tetrahydrofuran, dimethylformamide and certain aliphatic ketones.

In a preferred embodiment of the invention, the alcohol ZOH is methanol and the 5(RS)-methoxy-2,5-dihydrofuran-2-one is reacted with diphenyl isopropylidene sulfurane to obtain (1RS, 5SR) 6,6-dimethyl-4(RS)-methoxy-3-oxabicyclo (3,1,0) hexan-2-one which is then subjected to acid hydrolysis to obtain (1RS, 5SR) 6,6-dimethyl-4(RS)-hydroxy-3-oxabicyclo (3,1,0) hexan-2-one.

In another preferred embodiment of the invention, S-(α-methyl-3-phenoxyphenyl)-methanol is reacted with 5RS-hydroxy-2,5-dihydrofuran-2-one to obtain a mixture of 5R-[1S-(3-phenoxyphenyl)-α-methylmethoxy]-2,5-dihydrofuran-2-one and 5S-[1S-(3-phenoxyphenyl)-α-methylmethoxy]-2,5-dihydrofuran-2-one richer in the 5R isomer than the 5S isomer, separating the mixture by chromatography, reacting the 5R isomer with diphenylisopropylidene sulfurane to obtain (1R, 5S) 6,6-dimethyl-4R-[1S-(3-phenoxyphenyl)-α-methylmethoxy]-3-oxabicyclo (3,1,0) hexan-2-one and optionally subjecting the latter to acid hydrolysis to form (1R, 5S), 6,6-dimethyl-4R-hydroxy-3-oxabicyclo (3,1,0) hexan-2-one.

In a modification of the latter process, after the chromatographic separation, the 5S isomer is reacted with diphenylisopropylidene sulfurane to obtain (1S,5R) 6,6-dimethyl-4S-[1S-(3-phenoxyphenyl)-α-methylmethoxy]-3-oxabicyclo (3,1,0) hexan-2-one and optionally subjecting the latter to acid hydrolysis to obtain (1S, 5R) 6,6-dimethyl-4S-hydroxy-3-oxabicyclo (3,1,0) hexan-2-one.

In a further embodiment of the process of the invention, l-menthol is reacted with 5RS-hydroxy-2,5-dihydrofuran-2-one to obtain a mixture of 5R-[1R, 2S, 5R] 2-prop-2-yl-5-methylcyclohexyloxy-2,5-dihydrofuran-2-one and 5S [1R, 2S,5R]-2-prop-2-yl-5-methylcyclohexyloxy-2,5-dihydrofuran-2-one richer in the 5R isomer than the 5S isomer, separating the isomers by crystallization, reacting the 5R isomer with diphenylisopropylidene sulfurane to obtain (1R, 4R, 5S) 6,6-dimethyl-4-[(1R,2S,5R)-2-prop-2-yl-5-methylcyclohexyloxy]-3-oxabicyclo (3,1,0) hexan-2-one and optionally subjecting the latter to acid hydrolysis to obtain (1R, 5S) 6,6-dimethyl-4R-hydroxy-3-oxabicyclo (3,1,0) hexan-2-one.

In a modification of the latter embodiment of the process of the invention, after separation by crystallization, the 5S isomer is isolated by chromatography and reacted with diphenylisopropylidene sulfurane to obtain (1S, 4S, 5R) 6,6-dimethyl-4-[1R, 2S, 5R)-2-propy-2-yl-5-methyl-cyclohexyloxy]-3-oxabicyclo (3,1,0) hexan-2-one and optionally subjecting the latter to acid hydrolysis to obtain (1S, 5R) 6,6-dimethyl-4S-hydroxy-3-oxabicyclo (3,1,0) hexan-2-one.

In the process of the invention, analytical methods such as chromatography in high performance liquid phase (H.P.L.C.) permit one to know that the reaction of an optically active chiral alcohol with 5RS-hydroxy-2,5-dihydrofuran-2-one results in an asymmetric induction whereby the raw reaction product is richer in one of the two diastereoisomers than the other. For example, in the case of the ethers of S α-methyl-3-phenoxyphenyl methanol, the ratio of $$\frac{R \text{ isomer}}{R \text{ isomer} + S \text{ isomer}} = 67\%$$

instead of the theoretical 50% and in the case of ethers of l-menthol, the said ratio equals 59%. The existence of these 2 cases of asymetric induction shows that the choice of a chiral alcohol permits the obtention of a mixture richer in the desired stereochemical form and aids to isolate only this form.

It is noted that in the case of the ether of l-menthol, after separation of 5R [1R, 2S, 5R] 2-prop-2-yl-5-methylcyclohexyloxy-2,5-dihydrofuran-2-one, the resulting mother liquors after heating in an acid media lead to a new mixture of the R isomer and the S isomer in a proportion which is close to that of the initial mixture. One can repeat the procedure and thus isolate again the R isomer and obtain in several successive operations, a high yield of the R isomer.

This phenomenon is general for physical methods such as crystallization or chromatography to separate the two stereoisomer forms after which the mother liquors are heated in an acid media to obtain a new initial equilibrium of the R and S forms which can again be separated. Repetition of this procedure permits one to obtain a higher yields of one of the stereoisomer forms.

The stereoselectivity of the reaction of the sulfurane with the compounds of formula II is a particular advantage which permits the obtention of the compounds of formula I in only the desired stereoisomer form without any side reactions. Without limiting the scope of the invention, it is believed that the stereoselectivity of the reaction is due to the primary attack of the sulfurane on the 4-carbon atom of the furanone which uniquely is in the trans form with respect to the 5-OZ group. The final cyclization leads to a bicyclohexyl (3,1,0) derivative of the cis structure with the group OZ being exo. Finally, since the compounds of formula I contain 3 asymetric centers, the process of the invention results in a racemate when the alcohol Z-OH used is achiral or one of two corresponding enantiomorphs when the alcohol ZOH is chiral and which can be separated from the starting two diastereoisomeric ethers of 5-hydroxy-2,5-dihydrofuran-2-one.

The process of the invention has great advantages in that the starting materials are simple and inexpensive and in requiring only two reaction steps to permit access to the desired stereoisomeric forms of ethers of (1,5) 6,6-dimethyl-4-hydroxy-3-oxabicyclo (3,1,0) hexan-2-one and by hydrolysis, the stereoisomer forms of the corresponding 4-hydroxy derivatives.

Among the novel products of the invention are all the stereoisomeric forms, in the pure state or in the form of mixtures of the ethers obtained by the reaction of the compound of formula II and ZOH wherein Z is other than methyl or ethyl as well as the compounds of formula I wherein Y is other than methyl or ethyl.

In the following examples there are described several preferred embodiments to illustrate the invention. However, it should be understood that the invention is not intended to be limited to the specific embodiments.

EXAMPLE 1

(1RS, 5SR) 6,6-dimethyl-4-(RS)-methoxy-3-oxabicyclo [3,1,0] hexan-2-one 2 ml of a solution of 1.6M of tert.-butyllithium in pentane was added dropwise at −70° C. under an inert atmosphere to a stirred mixture of 950 mg of the tetrafluoroborate of isopropyldiphenylsulfonium in 15 ml of tetrahydrofuran and the mixture was stirred at −70° C. for 30 minutes to obtain a solution of diphenylisopropylidene sulfurane. The said solution at −70° C. was added slowly with stirring under an inert atmosphere to a mixture of 350 mg of 5(RS) methoxy-2,5-dihydrofuran-2-one [prepared by method of Schroeter et al, Liebigs Ann. Chem., Vol. 697 (1966), p. 42] and 15 ml of tetrahydrofuran cooled to −90° C. and the mixture was allowed to stand at −78° C. for one hour and then at −50° C. for another hour. The mixture was poured into an aqueous monosodium phosphate solution and the mixture was extracted with methylene chloride. The organic phase was evaporated to dryness under reduced pressure and the residue was chromatographed over silica gel. Elution with a 1-1 ether-petrolum ether mixture yielded 480 mg of diphenyl sulfide, 260 mg of (1RS, 5SR) 6,6-dimethyl-4(RS)-methoxy-3-oxabicyclo [3,1,0]-hexan-2-one and 100 mg of unreacted lactone.

EXAMPLE 2

(1R, 5S) 6,6-dimethyl-4(R)-[1S-(3-phenoxyphenyl)-α-methylmethoxy]-3-oxabicyclo [3,1,0] hexan-2-one

STEP A:

5R-[1S-(3-phenoxyphenyl)-α-methylmethoxy]-2,5-dihydrofuran-2-one

A mixture of 6.5 g of (S)α-methyl-(3-phenoxyphenyl)methanol, 3.5 g of 5-(RS)-hydroxy-2(5H)-furane, 180 mg of p-toluene sulfonic acid and 100 ml of anhydrous benzene was refluxed with stirring for 3 hours and was then cooled and neutralized with triethylamine. The mixture was evaporated to dryness under reduced pressure and the 10 g of oily residue were chromatographed over silica gel. Elution with a 95-5 benzene-ethyl acetate mixture yielded 5.3 g of 5-R-[1S-(3-phenoxyphenyl)-α-methylmethoxy]-2,5-dihydrofuran-2-one and then 2 g of 5S-[1S-(3-phenoxyphenyl)-α-methylmethoxy]-2,5-dihydrofuran-2-one.

NMR Spectrum (CDCl$_3$): 5-R isomer: peaks at 6.07–6.17 ppm (3-hydrogen of heterocycle); at 6.84–7.5 ppm (4-hydrogen of heterocycle); at 5.72 ppm (5-hydrogen of heterocycle); at 1.47–1.57 ppm (hydrogens of methyl); at 4.77–4.87–4.97–5.07 ppm (benzyl hydrogen); at 6.83 to 7.55 ppm (hydrogens of aromatic ring).

NMR Spectrum (CDCl$_3$): 5-S isomer: peaks at 1.41–1.48 ppm (hydrogens of methyl); at 4.66–4.76 ppm and 4.87–4.96 ppm (benzyl hydrogens); at 6.08 ppm (2-hydrogen of furanone); at 6.06–6.16 ppm (4-hydrogen of furanone); at 6.75–7.4 ppm (3-hydrogen of furanone); at 6.75 to 7.4 ppm (hydrogens of aromatic ring).

STEP B: (1R, 5S) 6,6-dimethyl-4(R)-[1S-(3-phenoxyphenyl)-α-methylmethoxy]-3-oxabicyclo (3,1,0) hexan-2-one A solution of ≈2.07M of diphenyl isopropylidene sulfurane (prepared from 655 mg of the fluoroborate of isopropyl diphenyl sulfonium and 1.5 ml of tert.-butyllithium) was slowly added at −70° C. with stirring under an inert atmosphere to a mixture of 400 mg of the 5R-isomer of Step A in 15 ml of tetrahydrofuran and the mixture was stirred at −70° C. for one hour and was then poured into aqueous monosodium phosphate solution. The mixture was extracted with methylene chloride and the organic phase was washed with water, dried and evaporated to dryness. The residue was crystallized from a 7-3 petroleum ether-ether mixture to obtain 310 mg of (1R, 5S) 6,6-dimethyl-4(R)-[1S-(3-phenoxyphenyl)-α-methylmethoxy]-3-oxabicyclo (3,1,0) hexan-2-one melting at 110° C.

Using the same procedure starting with the 5S isomer of Step A, the product was purified by chromatography over silica gel and elution with a 7-3 petroleum ether-ether mixture to obtain (1S, 5R) 6,6-dimethyl-4(S)-[1S-(3-phenoxyphenyl)-α-methylmethoxy]-3-oxabicyclo (3,1,0) hexan-2-one.

EXAMPLE 3

(1R, 5S) 6,6-dimethyl-4R-hydroxy-3-oxabicyclo (3,1,0) hexan-2-one

A mixture of 2 g of the (1R, 5S) product of Example 2, 20 ml of acetone and 5 ml of N aqueous hydrochloric acid was stirred at 20°–25° C. for 2 hours and was cooled to 0° to 5° C. The pH was adjusted to about 8 with sodium bicarbonate addition and the mixture was washed with benzene to remove α-methyl-3-phenoxybenzyl alcohol. The pH was adjusted to 1.5 to 2 by addition of concentrated hydrochloric acid and the mixture was extracted with ethyl acetate. The organic phase was washed with water, dried and evaporated to dryness under reduced pressure to obtain 800 mg of (1R, 5S) 6,6-dimethyl-4R-hydroxy-3-oxabicyclo (3,1,0) hexan-2-one melting at 120° C. and having specific rotation of $[\alpha]_D^{20} = -110°$ (c=1% in dimethylformamide).

EXAMPLE 4

(1R, 4R, 5S) 6,6-dimethyl-4-[(1R, 2S, 5R) 2-prop-2-yl-5-methylcyclohexyloxy]-3-oxabicyclo (3,1,0) hexan-2-one STEP A: 5R-[(1R, 2S, 5R)-2-prop-2-yl-5-methyl-cyclohexyloxy]-2,5-dihydrofuran-2-one A mixture of 32.5 g of p-menthol, 21 g of 5-hydroxy-2,5-dihydrofuran-2-one, 0.2 ml of p-toluene sulfonic acid and 300 ml of benzene was refluxed while azeotropically removing the water of reaction formed and then 4 g of 5-hydroxy-2,5-dihydrofuran-2-one were added thereto. The mixture was refluxed for another hour and was then cooled, washed with an aqueous sodium bicarbonate solution and then with water. The mixture was dried and evaporated to dryness under reduced pressure to obtain 51.6 g of resin. The latter was added to 100 ml of petroleum ether (b.p.=35°–70° C.) and the mixture was concentrated. The mixture stood at 0° C. for 17 hours and was vacuum filtered to obtain 15 g of crystals melting at 76° C. The mother liquors were evaporated to dryness and the residue was taken up in 150 ml of benzene. 200 mg of p-toluene sulfonic acid were added to the mixture which was then refluxed to remove the water of reaction azeotropically. The mixture was cooled and was washed with sodium bicarbonate solution and then with water, was dried and evaporated to dryness. The residue was crystallized from petroleum ether (b.p.=35°–70° C.) to obtain 10.35 g of product melting at 76° C. The mother liquors were subjected to an analogous treatment twice more for additional yields of 5.7 g and 3.4 g, respectively, of product melting at 76° C. for a total of 34.45 g of 5R-[(1R, 2S, 5R)-2-prop-2-yl-5-methyl-cyclohexyloxy]-2,5-dihydrofuran-2-one melting at 76° C. and having a specific rotation of $[\alpha]_D^{20} = -139°$ (c=1.5% in chloroform).

NMR Spectrum (deuterochloroform): peaks at 0.75–0.86 ppm, 0.86–1.0 ppm and 0.83–0.94 ppm (hydrogens of methyls of menthyl); at 3.66 ppm (1-hydrogen of menthyl); at 6.10–6.11–6.13 ppm (5-hydrogen of furanone); at 6.16–6.18 and 6.25–6.26 ppm (3-hydrogen of furanone); at 7.13–7.15 ppm and 7.21–7.23 ppm (4-hydrogen of furanone).

STEP B: (1R, 4R, 5S) 6,6-dimethyl-4-[(1R, 2S, 5R) 2-prop-2-yl-5-methyl-cyclohexyloxy]-3-oxabicyclo (3,1,0) hexan-2-one 1.2 ml of a solution of 1.5M of tert.-butyllithium in pentane was added all at once at −80° C. to a suspension of 500 mg of the fluoroborate of diphenylisopropyl phosphonium in 10 ml of tetrahydrofuran and the mixture was stirred at −80° C. for 30 minutes to obtain a solution of diphenyl isopropylidene sulfurane. The said solution was slowly added at −80° C. to a solution of 255 mg of the product of Step A in 10 ml of tetrahydrofuran and the mixture was stirred at −80° C. for one hour and was poured into a monosodium phosphate solution. The mixture was extracted with methylene chloride and the organic phase was washed with water, dried and evaporated to dryness. The residue was chromatographed over silica gel and was eluted with an 8-2 petroleum ether (b.p.=35°–70° C.)-ether mixture to obtain 220 mg of (1R, 4R, 5S) 6,6-dimethyl-4-[(1R, 2S, 5R) 2-prop-2-yl-5-methyl-cyclohexyloxy]-3-oxabicyclo (3,1,0) hexan-2-one melting at 82° C. and having a specific rotation of $[\alpha]_D^{20} = -195°$ (c=4% in chloroform).

NMR Spectrum ((CDCl$_3$)): Peaks at 0.73-1.0 ppm (hydrogens of 6-CH$_3$ of menthyl and hydrogens of methyls of 2-isopropyl of menthyl); at 1.15-1.2 ppm (hydrogens of 6-methyls of cyclopropyl ring); at 2.0 ppm (1- and 5-hydrogens of cyclopropyl ring); at 3.53 ppm (1-hydrogen of menthyl); at 5.32 ppm (4-hydrogens of lactone ring).

EXAMPLE 5

(1R, 4R, 5S) 6,6-dimethyl-4-hydroxy-3-oxabicyclo (3,1,0) hexan-2-one 8 ml of 0.5N hydrochloric acid solution were slowly added to a solution of 805 mg of the product of Example 4 in 8 ml of acetone and the mixture was stirred for 4 hours at 20° C. and was washed a plurality of times with petroleum ether (b.p.=35°-70° C.) to remove menthol. The aqueous phase was evaporated to dryness to obtain 360 mg of (1R, 4R, 5S) 6,6-dimethyl-4-hydroxy-3-oxabicyclo (3,1,0) hexan-2-one melting at 116°-120° C. and having a specific rotation of $[\alpha]_D^{20} = -114°$ (c=1% in dimethylformamide). Evaporation of the petroleum ether wash liquors resulted in a practically quantitative yield.

Various modifications of the products and process of the invention may be made without departing from the spirit or scope thereof and it should be understood that the invention is intended to be limited only as defined in the appended claims.

What is claimed is:

1. In the form of pure isomers or in the form of racemic mixtures in the 5-position, the compounds of the formula

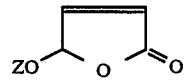

wherein Z is chiral and is selected from the group consisting of cyclohexyl substituted with alkyl of 1 to 4 carbon atoms and benzyl substituted on the α-methyl with methyl and on the phenyl with phenoxy.

* * * * *